United States Patent
Ichim et al.

(10) Patent No.: US 10,842,815 B2
(45) Date of Patent: Nov. 24, 2020

(54) PERISPINAL PERFUSION BY ADMINISTRATION OF T REGULATORY CELLS ALONE OR IN COMBINATION WITH ANGIOGENIC CELL THERAPIES

(71) Applicant: Creative Medical Technologies, Inc., Phoenix, AZ (US)

(72) Inventors: Thomas Ichim, San Diego, CA (US); Amit Patel, Salt Lake City, UT (US)

(73) Assignee: Stemspine LLC

( * ) Notice: Subject to any disclaimer, the term of this patent is extended or adjusted under 35 U.S.C. 154(b) by 36 days.

(21) Appl. No.: 16/009,982

(22) Filed: Jun. 15, 2018

(65) Prior Publication Data

US 2018/0360882 A1    Dec. 20, 2018

Related U.S. Application Data

(60) Provisional application No. 62/520,773, filed on Jun. 16, 2017.

(51) Int. Cl.
| | |
|---|---|
| *A61K 35/17* | (2015.01) |
| *A61K 35/28* | (2015.01) |
| *A61K 9/00* | (2006.01) |
| *C12N 5/0783* | (2010.01) |
| *C07K 14/71* | (2006.01) |
| *C07K 14/435* | (2006.01) |
| *A61K 38/45* | (2006.01) |
| *A61K 38/22* | (2006.01) |
| *A61K 38/19* | (2006.01) |
| *A61P 25/00* | (2006.01) |

(52) U.S. Cl.
CPC ............ *A61K 35/17* (2013.01); *A61K 9/0019* (2013.01); *A61K 35/28* (2013.01); *A61K 38/193* (2013.01); *A61K 38/22* (2013.01); *A61K 38/45* (2013.01); *A61P 25/00* (2018.01); *C07K 14/435* (2013.01); *C07K 14/71* (2013.01); *C12N 5/0637* (2013.01); *C12Y 207/10* (2013.01); *C12N 2500/02* (2013.01); *C12N 2501/165* (2013.01); *C12N 2501/998* (2013.01)

(58) Field of Classification Search
None
See application file for complete search history.

(56) References Cited

U.S. PATENT DOCUMENTS

| | | | |
|---|---|---|---|
| 9,598,673 B2 * | 3/2017 | Ichim | A61K 38/18 |
| 10,383,895 B2 * | 8/2019 | Ichim | A61K 35/17 |
| 2017/0239293 A1 * | 8/2017 | Ichim | C12N 5/0637 |

\* cited by examiner

*Primary Examiner* — Daniel C Gamett
(74) *Attorney, Agent, or Firm* — Baumgartner Patent Law; Marc Baumgartner

(57) ABSTRACT

Disclosed are method of enhancing perispinal perfusion in a patient suffering from reduced perfusion of the lower back through administration of T regulatory cells alone capable of stimulating angiogenesis directly or through enhancement of angiogenic activities of cellular therapies. Said cellular therapies possessing angiogenic activities include mesenchymal stem cells, hematopoietic stem cells and endothelial progenitor cells. In one embodiment of the invention, administration of T regulatory cells is performed that are expanded ex vivo. For certain embodiment of the invention T regulatory cells may be autologous or allogeneic.

20 Claims, No Drawings

PERISPINAL PERFUSION BY ADMINISTRATION OF T REGULATORY CELLS ALONE OR IN COMBINATION WITH ANGIOGENIC CELL THERAPIES

CROSS-REFERENCE TO RELATED APPLICATIONS

This application claims benefit of U.S. Provisional Application No. 62/520,773, filed Jun. 16, 2017, which is hereby incorporated by reference in its entirety.

FIELD OF THE INVENTION

The invention pertains to the field of lower back pain therapy, more particularly the invention relates to treatment of lower back pain by administration of anti-inflammatory immune cells termed T regulatory cells, more specifically the invention relates to the field of stimulating therapeutic angiogenesis in patients suffering from lower back pain who possess perfusion defects in order to overcome said perfusion defects through administration of angiogenic cells and supportive cells for angiogenesis.

BACKGROUND

T regulatory cells are an essential component of the immune system protecting the body against autoimmune attack [1-10]. This is illustrated by early studies in which neonatally thymectomized mice suffered from systemic autoimmunity, which were rescued by transfer of CD4 cells [11, 12]. Subsequent studies identified the T regulatory (Treg) phenotype as possessing the IL-2 receptor CD25, which is somewhat problematic given that this receptor is found on activated T cells as well [13]. Peripheral blood contains a small population of T cell lymphocytes that express the T regulatory phenotype ("Treg"), i.e., positive for both CD4 and CD25 antigens. There are several subsets of Treg cells. One subset of regulatory cells develops in the thymus. Thymic derived Treg cells function by a cytokine-independent mechanism, which involves cell to cell contact. They are essential for the induction and maintenance of self-tolerance and for the prevention of autoimmunity. These regulatory cells prevent the activation and proliferation of autoreactive T cells that have escaped thymic deletion or recognize extrathymic antigens, thus they are critical for homeostasis and immune regulation, as well as for protecting the host against the development of autoimmunity. Thus, immune regulatory CD4+ CD25+ T cells are often referred to as "professional suppressor cells."

Naturally arising CD4+ CD25+ Treg cells are a distinct cell population of cells that are positively selected on high affinity ligands in the thymus and that have been shown to play an important role in the establishment and maintenance of immunological tolerance to self antigens. Deficiencies in the development and/or function of these cells have been associated with severe autoimmunity in humans and various animal models of congenital or induced autoimmunity.

Treg cells manifest their tolerogenic effects directly via cell-to-cell contact or indirectly via soluble factors. Although the suppressive mechanisms of these cells remain to be fully elucidated, blockade of IL-2 expression in effector T cells (Teff), physical elimination of Teff cells, induction of tolerogenic dendritic cells (DCs) via CTLA-4/B7 axis, and inhibition of Teff cells via TGF-.beta. and IL-10 are some of the mechanisms that have been implicated to date. It also has been shown that reverse signaling through CTLA-4/CD80 into Teff cells plays an important role in their inhibition by Treg cells. Similarly, interactions between CTLA-4 on Treg cells and CD80 on DCs can result in reverse signaling and upregulation of the indoleamine dioxygenase enzyme that is involved in tolerance via the regulation of tryptophan metabolism.

SUMMARY

Embodiments herein are directed to methods of stimulating an increase in perfusion of the lower back area comprising the steps of: a) identifying a patient with a perfusion defect in said lower back area; b) administering a population of T regulatory cells in muscles surrounding the lower back area at a concentration and frequency sufficient to induce an angiogenic response.

According to preferred embodiments herin, the cell administration into said muscles surrounding the lower back is performed by intramuscular administration into muscles in the lumbar area selected from the group consisting of: a) Multifidus muscles; b) Psoas muscles; c) Transversospinalis muscles; d) Sacrospinalis muscles.

DESCRIPTION OF THE INVENTION

The invention The invention provides means of utilizing T regulatory cells for stimulation of angiogenesis in ischemic lumbar tissue for the purpose of stimulation endogenous regenerative processes in the disc. The invention teaches that stimulation of angiogenesis using T regulatory cells is useful for alleviating pain caused by irritation associated with accumulation of metabolites in conditions where there is reduced perfusion of the lumbar area. Furthermore, the anti-inflammatory activities of T regulatory cells are useful for reducing inflammation associated with lumbar ischemia, which inhibits activity of mesenchymal stem cells at inducing regeneration of degenerated discs.

In one embodiment the invention teaches the use of non-matched cord blood derived T regulatory cells for treatment of patients with lower back pain. The present invention includes compositions of expanded T regulatory cells (Tregs), and natural T regulatory cells (nTregs) for use in stimulation of lumbar angiogenesis. More preferably, the expanded cells retain nTreg or Treg phenotype and angiogenic activity following expansion and intramuscular administration into muscles associated with the lumbar area.

The invention provides compositions and methods for expanding Tregs, or Tregs, without the subsequent reversion of the nTregs to T effector cells after administration intramuscularly into lumbar associated muscles. Accordingly, such an expansion methodology allows for the establishment of a cell bank useful for stimulation of angiogenesis. In one aspect of the present invention, nTreg expansion can be performed by isolating nTregs from a desired cell source and subsequently culture expanding the cells in the presence of a primary signal and a co-stimulatory signal. Agents useful for stimulating a primary signal and an a co-stimulatory signal on Tregs may be used in soluble form, attached to the surface of a cell, or immobilized on a surface as described herein. In a preferred embodiment both primary and co-stimulatory agents are co-immobilized on a surface, for example a bead or an engineered cell. In one embodiment, the molecule providing the primary activation signal, such as a CD3 ligand, and the co-stimulatory molecule, such as a CD28 ligand are coupled to or loaded on the same surface, for example, a particle or an engineered cell. Said cells can be administered alone or with angiogenic cells to treat ischemic disorders.

In another embodiment, the invention provides a method of expanding Tregs, or nTregs to clinically useful numbers using a repetitive stimulation procedure. In one embodiment, the method of expanding nTregs comprises restimulating nTregs based upon cell size. Preferably, nTregs exhibiting a cell size about the size of a resting nTreg are chosen for restimulation. In some instances, the size of a resting nTreg is about 8.5 .mu.m. That is, the invention is based on the discovery that cell size is a parameter that contributes to the success of expanding nTregs without losing nTreg phenotype and suppressor activity. In another embodiment, the method of expanding nTregs comprises restimulating nTregs in the presence of Rapamycin. Preferably, nTregs isolated from peripheral blood is re-stimulated in the presence of Rapamycin. That is, the invention is based on the discovery that Rapamycin contributes to the success of expanding nTregs isolated from peripheral blood without losing nTreg phenotype and suppressor activity. Preferably, the expanded cells of the invention maintain Foxp3 profile indicative of nTregs. In one embodiment, the population of expanded nTregs expresses specific natural Treg markers such as Foxp3 and Latency Associated Peptide (LAP), displayed Treg specific demethylation in the Foxp3 gene, and contain very few IL-2, IFN.gamma., IL-17 secreting cells. The expanded cells of the invention also are able to suppress limb loss in a xenogenic model of muscle ischemia. In other embodiments, at least a portion of the active cell population is stored for later implantation/infusion. The population may be divided into more than one aliquot or unit such that part of the population of nTregs is retained for later application while part is applied immediately to the patient. Moderate to long-term storage of all or part of the cells in a cell bank is also within the scope of this invention. For the purpose of the invention, Treg and nTreg may be interchangeable.

Generation of Treg cells for use within the context of the invention may be performed by numerous means known in the art, which are incorporated by reference. For example, U.S. Patent Application No. 20100310588 (to Bluestone J. A. et al.) discloses methods for producing autoantigen-specific regulatory T cells and methods for use of same. According to the teachings of 20100310588, T cells are derived from a subject or from a donor, CD25+CD4+ T regulatory (Treg) cells are selected by immuno-selection and cell sorting, the Treg cells are expanded ex vivo by the use of a TCR/CD3 activator (e.g. anti-CD3 antibody), a TCR costimulator activator (e.g. anti-CD28 antibody) and IL-2 and the expanded population of Treg cells are adoptively transferred to a subject for treatment of autoimmune responses (e.g. diabetes, GVHD, Lupus, etc.). U.S. Patent Application No. 20100260781 (to Murray L. A.) provides methods and compositions for expanding T regulatory cells ex vivo or in vivo using one or more serum amyloid P(SAP) agonists (e.g. SAP polypeptide). According to their teachings, the use of SAP agonists enriches for regulatory T cells and thus promotes regulatory T cell-mediated suppression of autoimmune disorders or conditions (e.g. diabetes, graft rejection, GVHD, etc.). U.S. Patent Application No. 20100092488 (to Suzumura A. et al.) provides methods for increasing the number of regulatory T cells by inhibiting midkine (MK). 20100092488 further provides methods for treatment or prevention of diseases (e.g. autoimmune diseases such as diabetes, lupus etc.) associated with the functional disorder of regulatory T cells comprising the administration of a midkine inhibitor. U.S. Patent Application No. 20090142308 (to Orban T. et al.) provides methods for treating autoimmune diseases (e.g. diabetes) by inducing autoantigen-specific regulatory CD4+ T cells. According to the teachings of 20090142308, treating an autoimmune disease is effected by first administering to the subject a composition comprising an autoantigen (e.g. insulin) and an oil-and-water adjuvant. Next, a blood sample comprising PBMCs is obtained from the subject and autoantigen-specific regulatory T cells are isolated therefrom. The autoantigen-specific regulatory T cells may then be expanded ex vivo to obtain an adequate amount of cells for treatment and the autoantigen-specific regulatory T cells are then administered back to a subject. PCT Publication No. 2010/017220 (to Kambayashi T. et al.) discloses methods of expanding and enriching a regulatory T-cell population by contacting a leukocytes population having antigen-presenting cells with a granulocyte-macrophage colony stimulating factor (GMCSF), interleukin-3 (IL-3) and/or interleukin-5 (IL-5). The regulatory T cells disclosed therein may be used for suppressing naive T-cells in a subject and subsequently for the treatment of autoimmune diseases.

In one embodiment Treg cells are generated by means that are known in various laboratories and routinely used. Any method of cell isolation may be used according to the present teachings. One exemplary method of isolation of regulatory cells from peripheral blood comprises centrifugation, with or without a gradient (e.g. Percoll gradient). This technique separates cells based upon density. Another exemplary method which may be used comprises panning and immunomagnetic isolation, using molecules immobilized to surface or magnetic beads, respectively, as for example, antibodies that recognize and bind molecules on the cell surface (e.g. CD4, CD8, CD20, etc.). Molecules immobilized to a surface or conjugated to magnetic beads recognize and bind to one or more of the cell specific surface markers of a particular cell type. Cells that possess one or more cell surface markers are bound by the immobilized molecules or exposure of the bead-conjugated cells to a magnetic field, allowing any other cell to be washed away. In positive selection procedures the cell type of interest is retained, and in negative selection procedures cell type of interest is purged. Another isolation procedure which may used according to the present teachings includes fluorescence activated cell sorting (FACS). Antibodies with fluorescent tags may be used to bind to the cells of interest. The antibodies bind to the cell surface molecules (e.g. CD4, CD8, CD20, etc.), and a FACS sorter may then sort and collect the cells based upon the fluorescence observed. The cells that display certain fluorescence may then be isolated. Following isolation of the immune regulatory cells, the cells may be further cultured, expanded and/or stimulated. Ex vivo expansion of isolated immune regulatory cells include, for example, the protocol for T regulatory cells: cells are cultured with CD3/CD28 stimulation (e.g. anti-CD3 antibody and anti-CD28 antibody) in the presence of high IL-2 concentrations, IL-10 and stimulation/education with dendritic cells. Ex vivo expansion of the cells as described herein (i.e. with an antigen presenting cell) may also selectively enrich for antigen-specific immune regulatory cells. It will be appreciated that the immune regulatory cells may also be expanded in vivo in order to increase the number of these cells prior to isolation and ex vivo manipulation.

In some embodiments of the invention, intramuscular administration of Treg cells is performed into the perispinal muscles together with an immune suppressant. This use of immune suppressant is particularly desirable when allogeneic Treg cells are utilized. Examples of immunosuppressive agents which may be used in conjunction with the invention, but are not limited to, steroids, rapamycin, fludarabin methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE ®), etanercept, TNF.alpha.. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

In some embodiments, Treg cells are expanded from cord blood. Protocols are known in the art for generation of clinically relevant numbers of cord blood derived Treg cells. Several examples are given below. "Fresh" CB (fresh is defined as processed within 48 hr of cord blood draw) can be collected as cord blood units (CBUs) containing 35 mL of citrate phosphate dextrose (CPD) anticoagulant. CBUs (n=11) which are processed for isolation of cord blood mononuclear cells (CBMCs) by density gradient centrifugation (Ficoll-Paque PLUS, GE Healthcare). CBUs are thawed and resuspended in 60 mL of dextran-HSA wash solution (divided into two 50-mL conical tubes), allowed to warm to room temperature, and underlaid with 15 mL Ficoll-Paque PLUS per conical tube for density gradient centrifugation and CBMC isolation. One protocol for Treg expansion is performed using FACS-isolated cells that are plated according. Antigen presenting cells (APC) were prepared from KT64/86, a K562-derived cell line constitutively expressing high-affinity Fc receptor, CD64, and CD86 for co-stimulation. Fc-binding receptors on KT64/86 were precleared of serum immunoglobulins by culture in serum-free medium (SFM) overnight and then irradiated at 10,000 rad. Anti-CD3 (clone OKT-3, Miltenyi Biotec) monoclonal antibody (mAb) was loaded on KT64/86 at 1 µg/$10^6$ cells at 4° C. for 30 min, washed twice with SFM, and cryopreserved in CryoStor CS10 (BioLife Solutions). After Treg FACS purification (described above), KT64/86 APCs are added to culture at a 1:1 aAPC-to-Treg cell ratio. CB Tregs and cryoCB Tregs can be expanded in complete RPMI 1640 (cRPMI)—consisting of RPMI 1640 (Life Technologies) supplemented with 10% FBS (Atlanta Biologicals), 1 M HEPES, 1 mM sodium pyruvate, 100× minimum essential medium (MEM) non-essential amino acid solution, 50 mM 2-mercaptoethanol (2-ME), and 100 U penicillin/streptomycin (Gibco)—plus 600 IU/mL Proleukin (human recombinant IL-2 [hrIL-2], Prometheus Laboratories). Tregs can then be expanded in cRPMI plus 300 IU/mL Proleukin (hrIL-2, Prometheus Laboratories). On day 2, the culture volume is doubled, and IL-2 is added (at the aforementioned concentrations, assuming consumption). Cells are resuspended, and fresh medium and IL-2 were added on days 4, 6, 8, 11, and 13. On day 9, cells are restimulated with Dynabeads (human T-activator CD3/CD28 for T cell expansion and activation, Dynal Invitrogen) at a 1:1 ratio. Another protocol involves FACS-isolated cells that are plated evenly at $2.5 \times 10^4$ to $5.0 \times 10^4$ Tregs/well in a 96-well flat-bottom plate (Costar) and activated with anti-CD3/anti-CD28-coated microbeads (MACS GMP ExpAct Treg kit for research use, Miltenyi Biotec) at a 4:1 bead-to-cell ratio. CB Tregs and cryoCB Tregs are expanded in cRPMI plus 600 IU/mL Proleukin (hrIL-2, Prometheus Laboratories). APB Tregs are expanded in cRPMI plus 300 IU/mL Proleukin (hrIL-2, Prometheus Laboratories). On day 2, the culture volume is doubled, and fresh IL-2 is added (at the aforementioned concentrations, assuming consumption). Cells are resuspended, and fresh medium and IL-2 is added on days 4, 6, 8, 11, 13, 15, 17, 20, 22, 24, and 26, assuming consumption. On days 9 and 18, cells are restimulated with fresh anti-CD3/anti-CD28-coated beads at a 1:1 ratio.

Another protocol involves use of FACS-isolated cells that are plated and activated with Dynabeads at a 4:1 bead-to-cell ratio. Cells are cultured either in X-VIVO 15 or in X-VIVO 15 customized by Lonza by substituting 100% of the glucose in the base medium with D-glucose (6,6-2H2, 99%) (Cambridge Isotope Laboratories, catalog no. DLM-349-MPT) supplemented with 10% human heat-inactivated pooled APB serum. On day 2, the culture volume was doubled, and IL-2 was added (300 IU/mL, Proleukin). Cells were resuspended, and fresh medium and IL-2 were added (600 IU/mL, Proleukin) on days 5, 7, 12, and 14, assuming consumption. On day 9, cells were restimulated with additional Dynabeads at a 1:1 ratio.

For all generation of Treg it is important that final release criteria is followed. In one example, final release criteria involves cells being assessed for purity ($\leq$5% $CD8^+$ cells, <100 beads/$3 \times 10^6$ cells, and endotoxin $\leq$3.5 endotoxin units [EU]/mL), phenotype ($\geq$95% $CD4^+$ cells and $\geq$60% $FOXP3^+$), sterility (negative for mycoplasma, anaerobic and aerobic bacteria, gram stain, fungal culture, potassium hydroxide [KOH] exam), and viability ($\geq$85%) [14].

Other methods of expanding and clinically using Treg cells have been reported and are incorporated by reference. For example, McKenna et al used artificial (aAPC) to grow cord blood derived Treg. They found that aAPCs increased UCB tTreg expansion greater than eightfold over CD3/28 stimulation. Re-stimulation with aAPCs increased UCB tTreg expansion an additional 20- to 30-fold. Re-stimulated human UCB tTreg ameliorated GVHD disease in a xenogeneic model. Following current Good Manufacturing Practice (cGMP) validation, a trial was conducted with tTreg. tTreg doses up to >30-fold higher compared with that obtained with anti-CD3/28 mAb coated-bead expansion and Foxp3 expression was stable during in vitro expansion and following transfer to patients. Increased expansion did not result in a senescent phenotype and GVHD was significantly reduced [15]. Safinia et al reported the manufacture of clinical grade Tregs from prospective liver transplant recipients via a CliniMACS-based GMP isolation technique and expanded using anti-CD3/CD28 beads, IL-2 and rapamycin. They reported the enrichment of a pure, stable population of Tregs (>95% CD4(+)CD25(+)FOXP3(+)), reaching adequate numbers for their clinical application. The protocol proved successful in, influencing the expansion of superior functional Tregs, as compared to freshly isolated cells, whilst also preventing their conversion to Th17 cells under pro-inflammatory conditions [16]. In one embodiment of the invention Treg cells that are generated, either in vitro or in vivo are further augmented in activity by modulation of the host microbiome. Modulation of microbiome may be performed by administration of either probiotics and/or prebiotics. It is known in the art that the intestinal microbiota drives host immune homeostasis by regulating the differentiation and expansion of T reg, Th1, and Th2 cells. It has been demonstrate that $Foxp3^+$ T reg cell deficiency results in gut microbial dysbiosis and autoimmunity. Means of remodeling the microbiome are described in the art and include administration of *Lactobacillus reuteri*, which is associated in animal models of autoimmunity with prolonged survival and reduced multiorgan inflammation. In one embodiment of the invention *L. reuteri* is administered to change the metabolomic profile disrupted by T reg cell deficiency, and to restore levels of the purine metabolite inosine. Accordingly, in one embodiment of the invention administration of inosine together with generation of Treg cells is utilized to stimulate enhanced suppressive activity and thereby treatment of autoimmunity. Means of administering inosine and modulation of microbiome for augmentation of Treg cells are described in the following papers which are incorporated by reference [17-42].

Previous studies have demonstrated that mesenchymal stem cells (MSC) are capable of producing growth factors associated with cellular proliferation such as FGF [43, 44], VEGF [45-47], IGF-1 [48] and HGF [49]. In fact MSC feeder layers have previously been used to expand hematopoietic [50, 51], and pluripotent [52, 53], stem cells while maintaining these cells in an undifferentiated state. Furthermore, MSC have been demonstrated to promote generation of Treg cells in vitro [54-59], and in vivo [60-62]. In one embodiment of the invention Treg are expanded by culture with MSC in vitro or coinjected with MSC in vivo. In one embodiment, MSC are generated according to protocols previously utilized for treatment of patients utilizing bone marrow derived MSC. Specifically, bone marrow is aspirated (10-30 ml) under local anesthesia (with or without sedation) from the posterior iliac crest, collected into sodium heparin containing tubes and transferred to a Good Manufacturing Practices (GMP) clean room. Bone marrow cells are washed with a washing solution such as Dulbecco's phosphate-buffered saline (DPBS), RPMI, or PBS supplemented with autologous patient plasma and layered on to 25 ml of Percoll (1.073 g/ml) at a concentration of approximately $1\text{-}2 \cdot 10^7$ cells/ml. Subsequently the cells are centrifuged at 900 g for approximately 30 min or a time period sufficient to achieve separation of mononuclear cells from debris and erythrocytes. Said cells are then washed with PBS and plated at a density of approximately $1 \cdot 10^6$ cells per ml in 175 cm$^2$ tissue culture flasks in DMEM with 10% FCS with flasks subsequently being loaded with a minimum of 30 million bone marrow mononuclear cells. The MSCs are allowed to adhere for 72 h followed by media changes every 3-4 days. Adherent cells are removed with 0.05% trypsin-EDTA and replated at a density of $1 \cdot 10^6$ per 175 cm$^2$. Said bone marrow MSC may be administered intravenously, or in a preferred embodiment, intrathecally in a patient suffering radiation associated neurodegenerative manifestations. Although doses may be determined by one of skill in the art, and are dependent on various patient characteristics, intravenous administration may be performed at concentrations ranging from 1-10 million MSC per kilogram, with a preferred dose of approximately 2-5 million cells per kilogram.

The present invention includes a method of using MSC that have been cultured under conditions to express increased amounts of at least one anti-apoptotic protein as a therapy to inhibit or prevent apoptosis. In one embodiment, the MSC which are used as a therapy to inhibit or prevent apoptosis have been contacted with an apoptotic cell. The invention is based on the discovery that MSC that have been contacted with an apoptotic cell express high levels of anti-apoptotic molecules. In some instances, the MSC that have been contacted with an apoptotic cell secrete high levels of at least one anti-apoptotic protein, including but not limited to, STC-1, BCL-2, XIAP, Survivin, and Bcl-2XL. Methods of transfecting antiapoptotic genes into MSC have been previously described which can be applied to the current invention, said antiapoptotic genes that can be utilized for practice of the invention, in a nonlimiting way, include GATA-4 [63], FGF-2 [64], bcl-2 [65, 66], and HO-1 [67]. Based upon the disclosure provided herein, MSC can be obtained from any source. The MSC may be autologous with respect to the recipient (obtained from the same host) or allogeneic with respect to the recipient. In addition, the MSC may be xenogeneic to the recipient (obtained from an animal of a different species). In one embodiment of the invention MSC are pretreated with agents to induce expression of antiapoptotic genes, one example is pretreatment with exendin-4 as previously described [68]. In a further non-limiting embodiment, MSC used in the present invention can be isolated, from the bone marrow of any species of mammal, including but not limited to, human, mouse, rat, ape, gibbon, bovine. In a non-limiting embodiment, the MSC are isolated from a human, a mouse, or a rat. In another non-limiting embodiment, the MSC are isolated from a human.

Based upon the present disclosure, MSC can be isolated and expanded in culture in vitro to obtain sufficient numbers of cells for use in the methods described herein provided that the MSC are cultured in a manner that promotes contact with a tumor endothelial cell. For example, MSC can be isolated from human bone marrow and cultured in complete medium (DMEM low glucose containing 4 mM L-glutamine, 10% FBS, and 1% penicillin/streptomycin) in hanging drops or on non-adherent dishes. The invention, however, should in no way be construed to be limited to any one method of isolating and/or to any culturing medium. Rather, any method of isolating and any culturing medium should be construed to be included in the present invention provided that the MSC are cultured in a manner that provides MSC to express increased amounts of at least one anti-apoptotic protein. Culture conditions for growth of clinical grade MSC have been described in the literature and are incorporated by reference [69-102].

In one exemplary embodiment, diagnosed intravertebral hypoperfusion can be treated by increasing perfusion in identified area(s) such as by injection of Treg cells. In preferred embodiments, injection can be directly into the vertebral body to a location within and/or proximate to the identified area or areas of hypoperfusion. The identified area or areas can be accessed via one or more of the pedicles of the vertebral body with a surgical access and delivery device such as a surgical access needle extending through the patient's skin and overlying soft tissues in a minimally-invasive manner, extending through one or more pedicles and into the vertebral body located proximate to the vertebral endplate. The composition can then be introduced into the vertebral body through the delivery device.

In various embodiments, hypoxic and/or ischemic disc disease is treated by increasing perfusion in the affected area such as by injection of a composition that includes an angiogenic factor. In preferred embodiments, injection is around the vertebrae or directly into the vertebral body. In other embodiments, injection of angiogenic compounds may be positioned into and/or adjacent to other anatomical structures, including the annulus of the disc and/or arterioles. In some embodiments, a localized delivery system capable of forming a gel-like structure may be used to deliver the angiogenic factor. Preferably, the delivery system includes components of extracellular matrix that provide conditions suitable for angiogenesis. In some embodiments, said extracellular matrix components may be hyaluronic acid fragments. In other embodiments, said extracellular matrix components may be derivatives of collagen, or perlecan.

Preferably, the gel-like structure includes a polymer capable of slow release such as a poloxamer block copolymer (Pluronic®, BASF), basement membrane preparation (Matrigel®, BD Biosciences) or collagen-based matrix such as described by U.S. Pat. No. 6,346,515, which is incorporated herein by reference.

In various embodiments, hypoxic and/or ischemic disc disease can be treated by administration of a medical device that generates a continuous release of a composition which includes Treg cells along or in combination with cells or factors capable of stimulating angiogenesis, and specifically, collateralization in the area(s) proximal to hypoperfusion. In some embodiments, the composition could further include stem cells and/or other biological treatments, which might be used in conjunction with angiogenic factors prior to, during and/or subsequent to the employment of tissue grafts to repair or replace native tissues. If desired, such compositions could be used to prepare a patient's anatomical site for an intended tissue graft or surgical procedure, could be used to prepare the tissue graft for implantation, and/or could be used to treat the patient and/or tissue graft site after implantation. In various embodiments, a medical device may include a slow release pump such as an implantable indwelling or osmotic pump or a localized delivery system such as a polymer capable of slow release, as described herein. In an embodiment, the composition delivered by the medical device contains not only a therapeutically sufficient concentration of a growth factor that stimulates angiogenesis, but also a chemotactic agent. Some growth factors, such as fibroblast growth factor 1 (FGF-1), are themselves chemotactic. The chemotactic agent recruits cells capable of causing or promoting angiogenesis. In some embodiments, a chemotactic agent such as stromal cell-derived factor 1 (SDF-1) is included in the composition with the growth factor. In various embodiments, the composition delivered by the medical device may contain an anti-inflammatory agent at a concentration sufficient for inhibiting possible inflammatory reactions associated with neoangiogenesis, while at the same time not inhibiting collateral blood vessel formation. Depending upon the specific tissue structure(s) concerned, the diagnosis and/or treatment methods and systems described herein can include the selection and analysis of a plurality of relevant tissue structures. For example, where the diagnosis and/or treatment of a patient's intervertebral disc is of interest, the methods and systems described herein can include the imaging and analysis of intravertebral structures of vertebral bodies proximate to both the cephalad and caudad endplates of the intervertebral disc of interest. Depending upon the physician's preference and/or the relevant clinical situation, diagnosis of intravertebral hypoperfusion of either or both of the disc endplates may indicate a need for further treatment, as described herein. In various embodiments, assessment of perfusion can be performed, followed by therapy that increases the rate of perfusion, followed by a subsequent assessment of perfusion so as to identify the ideal conditions for stimulation of perfusion on an individualized basis.

In various embodiments, it may be desirous to treat an identified deficiency before significant disc degeneration and/or damage has occurred, even where the opposing endplate appears to be providing normal nutrition and waste removal. This can include imaging and analysis of anatomy proximate to both endplates of an intervertebral disc that can be performed to quantify whether one endplate should be treated alone or both endplates of a given disc together. If desired, the imaging data and analysis could provide an ability to compare not only each disc at risk, but also identify which endplate is the most contributing to the lack of perfusion for a specific level. This information could help in the treatment approach. In addition, the specific characteristics of the imaging data may demonstrate which vessels and/or intravertebral architecture may be susceptible to treatment versus other imaging data that shows capillaries and/or other structures that may be at a stage where treatment may not be as successful. In addition, coupling imaging data with endplate integrity data may provide insight as to how well the vessels would be predicted to grow into the exchange area of the vertebral body (i.e., proximate to the endplate) and disc and mature into functional capillaries capable of providing nutrient exchange and waste removal. Measuring the endplate and disc diffusion capabilities coupled with the endplate cartilaginous integrity and 2 or 3-D mapping of the endplate capillaries might outline the area, level, side of the disc and anterior or posterior aspect of the disc to be treated. FIG. 18 demonstrates a DCE-MRI mid-sagittal section of a lumbar spine (see also FIG. 17). The T12-L1 disc mid-sagittal data can be reconstructed to create an axial section 1 mm proximal to the vertebral endplate. This generated data maps the endplate into right, left, anterior and posterior sections for careful analysis of the greatest ischemic and/or hypoxic region or relative measures thereof.

Another embodiment may provide similar treatment for the intervertebral disc (or discs) that are already degenerative with components of this degeneration that may be due to endplate hypoxia or ischemia and the resultant decrease in the necessary nutrients for matrix repair. For the disc to "heal", the necessary pathway for the nutrients required for aerobic energy metabolism could be restored. This might entail delivery of Treg cells directly into the hypoperfused endplate. This treatment may be preoperatively planned with the proper imaging for mapping of the area to be treated. In addition, the Treg (and/or other angiogenic factors or other necessary constituents) can be injected or implanted or laid adjacent to the endplate using various delivery schemes depending upon the pharmacologic properties of the various angiogenic factors and the consistency and fluid dynamics of their formulations. The treated disc's healing environment may or may not be further enhanced with implants to "unload" the disc (or discs) if it is desired by the treating physician that a more optimal biomechanical environment could be achieved with this approach. The postoperative healing environment could be assessed with serial imaging studies and treatment could be modified if necessary. This modification could alter the biomechanical properties of the "un-loading" implant to either share more or less of the motion-segment load (i.e., two adjacent vertebrae with their intervening intervertebral disc and facet joints). This alteration could be done remotely with the proper materials and controls of the implant. In addition, further treatment with the angiogenic factor could be performed depending upon the clinical and imaging information in the postoperative period.

In various embodiments of the invention, a direct injection of Treg cells into the ischemic vertebral body could be performed to produce and/or induce angiogenesis within the vertebral body (and desirably the subchondral capillary bed that supplies the disc with its nutrients). The vertebral pedicle, a route used in pedicle screw spinal implants as well as vertebroplasty and kyphoplasty treatments of vertebral compression fractures, can easily be entered with a direct catheter for injection. The pedicle communicates with the vertebral body. The injection can be done percutaneously or with open surgery. This injection can be short term (one injection) or be delivered within an indwelling catheter for longer administration. In addition, a device could be introduced through the pedicle that can be placed within the vertebral body for long term introduction of Treg cell. In addition to the vertebral pedicle, direct placement into the vertebral body through the vertebral body cortical wall could be a method of delivering angiogenic factors to the vertebrae. This can be performed at the time of open surgery or via a percutaneous route.

In one embodiment of the invention, the stimulation of perfusion in the area proximal to a pain generator can result in improving disc nutrition so as to enhance healing and production of appropriate proteins in said disc. It is known that the synthesis of proteoglycans in the nucleus pulposus occurs naturally by the cellular component of the nucleus pulposus. Specific growth factors such as transforming growth factor-.beta. (TGF-.beta.) and epidermal growth factor (EGF) are involved in the stimulation of proteoglycan synthesis. In one embodiment Tregs are utilized to induce regeneration of proteoglycan synthesis. Interestingly, in patients with degenerative disc disease, the amount of these cytokines is reduced in comparison to healthy nucleus pulposus cells. This reduction may be due to decreased nutrient supply and cellular viability within said nucleus. Another reason for inhibition of proteoglycan synthesis is lower pH caused by ischemia and/or hypoperfusion of the lumbar area. The low pH also appears to be involved in another process associated with discogenic pain, said process comprising up regulation of matrix metalloproteases expression. It is known that matrix metalloproteases are involved in cleaving proteoglycans, and that up regulation of matrix metalloprotease activity is associated with disc degeneration. Activation of matrix metalloproteases is known to be induced by inflammatory cytokines such as TNF and IL-1. Additionally, animal studies have demonstrated that hyperphysiological loading of the disc segment induces up regulation of matrix metalloproteases, but have not assessed the influence of perfusion. Accordingly, in one embodiment of the invention, the increase of localized perfusion is used to augment proteoglycan content in said nucleus pulposus, as well as to lead to suppression, in some instances, of MMP activation.

The dose of Treg cells appropriate to be used in accordance with various embodiments of the invention will depend on numerous factors. It may vary considerably for different circumstances. The parameters that will determine optimal doses of Treg cells to be administered for primary and adjunctive therapy generally will include some or all of the following: the disease being treated and its stage; the species of the subject, their health, gender, age, weight, and metabolic rate; the subject's immunocompetence; other therapies being administered; and expected potential complications from the subject's history or genotype. The parameters may also include: whether the Treg cells are syngeneic, autologous, allogeneic, or xenogeneic; their potency (specific activity); the site and/or distribution that must be targeted for the Treg cells to be effective; and such characteristics of the site such as accessibility to Treg cells and/or engraftment of Treg cells. Additional parameters include co-administration with Treg cells of other factors (such as growth factors and cytokines). The optimal dose in a given situation also will take into consideration the way in which the cells are formulated, the way they are administered, and the degree to which the cells will be localized at the target sites following administration. Finally, the determination of optimal dosing necessarily will provide an effective dose that is neither below the threshold of maximal beneficial effect nor above the threshold where the deleterious effects associated with the dose of Treg cells outweighs the advantages of the increased dose.

The optimal dose of Treg cells for some embodiments will be in the range of doses used for autologous, mononuclear bone marrow transplantation. For fairly pure preparations of Treg cells, optimal doses in various embodiments will range from $10^4$ to $10^8$ Treg cells/kg of recipient mass per administration. In some embodiments the optimal dose per administration will be between $10^5$ to $10^7$ Treg cells/kg. In many embodiments the optimal dose per administration will be $5 \times 10^5$ to $5 \times 10^6$ Treg cells/kg. By way of reference, higher doses in the foregoing are analogous to the doses of nucleated cells used in autologous mononuclear bone marrow transplantation. It is to be appreciated that a single dose may be delivered all at once, fractionally, or continuously over a period of time. The entire dose also may be delivered to a single location or spread fractionally over several locations.

It is noted that human subjects are treated generally longer than experimental animals; but, treatment generally has a length proportional to the length of the disease process and the effectiveness of the treatment. Those skilled in the art will take this into account in using the results of other procedures carried out in humans and/or in animals, such as rats, mice, non-human primates, and the like, to determine appropriate doses for humans. Such determinations, based on these considerations and taking into account guidance provided by the present disclosure and the prior art will enable the skilled artisan to do so without undue experimentation.

Suitable regimens for initial administration and further doses or for sequential administrations may all be the same or may be variable. Appropriate regiments can be ascertained by the skilled artisan, from this disclosure, the documents cited herein, and the knowledge in the art.

REFERENCES

1. Bocian, K., et al., *Expanding Diversity and Common Goal of Regulatory T and B Cells. I: Origin, Phenotype, Mechanisms.* Arch Immunol Ther Exp (Warsz), 2017.
2. Ooi, J. D., et al., *Dominant protection from HLA-linked autoimmunity by antigen-specific regulatory T cells.* Nature, 2017. 545(7653): p. 243-247.
3. Melis, D., et al., *Cutting Edge: Increased Autoimmunity Risk in Glycogen Storage Disease Type 1b Is Associated with a Reduced Engagement of Glycolysis in T Cells and an Impaired Regulatory T Cell Function.* J Immunol, 2017. 198(10): p. 3803-3808.
4. Stojanovic, I., et al., *Cell-based tolerogenic therapy, experience from animal models of multiple sclerosis, type 1 diabetes and rheumatoid arthritis.* Curr Pharm Des, 2017.
5. Lee, P. W., M. E. Severin, and A. E. Lovett-Racke, *TGF-beta regulation of encephalitogenic and regulatory T cells in multiple sclerosis.* Eur J Immunol, 2017. 47(3): p. 446-453.
6. Engler, J. B., et al., *Glucocorticoid receptor in T cells mediates protection from autoimmunity in pregnancy.* Proc Natl Acad Sci U S A, 2017. 114(2): p. E181-E190.
7. Haque, M., et al., *Development of Stem Cell-derived Antigen-specific Regulatory T Cells Against Autoimmunity.* J Vis Exp, 2016(117).
8. Fouad, H., et al., *Regulatory and activated effector T cells in chronic hepatitis C virus: Relation to autoimmunity.* World J Hepatol, 2016. 8(30): p. 1287-1294.

9. Azizi, G., et al., *Cellular and molecular mechanisms of immune dysregulation and autoimmunity.* Cell Immunol, 2016. 310: p. 14-26.
10. Arellano, B., D. J. Graber, and C. L. Sentman, *Regulatory T cell-based therapies for autoimmunity.* Discov Med, 2016. 22(119): p. 73-80.
11. Bagavant, H., et al., *Differential effect of neonatal thymectomy on systemic and organ-specific autoimmune disease.* Int Immunol, 2002. 14(12): p. 1397-406.
12. Kim, J. M. and A. Rudensky, *The role of the transcription factor Foxp3 in the development of regulatory T cells.* Immunol Rev, 2006. 212: p. 86-98.
13. Suri-Payer, E., et al., *CD4+CD25+ T cells inhibit both the induction and effector function of autoreactive T cells and represent a unique lineage of immunoregulatory cells.* J Immunol, 1998. 160(3): p. 1212-8.
14. Bluestone, J. A., et al., *Type 1 diabetes immunotherapy using polyclonal regulatory T cells.* Sci Transl Med, 2015. 7(315): p. 315ra189.
15. McKenna, D. H., Jr., et al., *Optimization of cGMP purification and expansion of umbilical cord blood-derived T-regulatory cells in support of first-in-human clinical trials.* Cytotherapy, 2017. 19(2): p. 250-262.
16. Safinia, N., et al., *Successful expansion of functional and stable regulatory T cells for immunotherapy in liver transplantation.* Oncotarget, 2016. 7(7): p. 7563-77.
17. He, B., et al., *Resetting microbiota by Lactobacillus reuteri inhibits T reg deficiency-induced autoimmunity via adenosine A2A receptors.* J Exp Med, 2017. 214(1): p. 107-123.
18. Hrdy, J., et al., *The effect of a probiotic Escherichia coli strain on regulatory T-cells in six year-old children.* Benef Microbes, 2016. 7(5): p. 639-648.
19. Thakur, B. K., et al., *Live and heat-killed probiotic Lactobacillus casei Lbs2 protects from experimental colitis through Toll-like receptor 2-dependent induction of T-regulatory response.* Int Immunopharmacol, 2016. 36: p. 39-50.
20. Haileselassie, Y., et al., *Postbiotic Modulation of Retinoic Acid Imprinted Mucosal-like Dendritic Cells by Probiotic Lactobacillus reuteri 17938 In Vitro.* Front Immunol, 2016. 7: p. 96.
21. Liu, Y., et al., *Lactobacillus reuteri DSM 17938 differentially modulates effector memory T cells and Foxp3+ regulatory T cells in a mouse model of necrotizing enterocolitis.* Am J Physiol Gastrointest Liver Physiol, 2014. 307(2): p. G177-86.
22. Kim, H. J., et al., *Effects of Lactobacillus rhamnosus on allergic march model by suppressing Th2, Th17, and TSLP responses via CD4(+)CD25(+)Foxp3(+) Tregs.* Clin Immunol, 2014. 153(1): p. 178-86.
23. Narushima, S., et al., *Characterization of the 17 strains of regulatory T cell-inducing human-derived Clostridia.* Gut Microbes, 2014. 5(3): p. 333-9.
24. Mercadante, A. C., et al., *Oral combined therapy with probiotics and alloantigen induces B cell-dependent long-lasting specific tolerance.* J Immunol, 2014. 192(4): p. 1928-37.
25. Yoshida, T., et al., *An increased number of CD4+CD25+ cells induced by an oral administration of Lactobacillus plantarum NRIC0380 are involved in antiallergic activity.* Int Arch Allergy Immunol, 2013. 162(4): p. 283-9.
26. Barletta, B., et al., *Probiotic VSL#3-induced TGF-beta ameliorates food allergy inflammation in a mouse model of peanut sensitization through the induction of regulatory T cells in the gut mucosa.* Mol Nutr Food Res, 2013. 57(12): p. 2233-44.
27. Smelt, M. J., et al., *Probiotics can generate FoxP3 T-cell responses in the small intestine and simultaneously inducing CD4 and CD8 T cell activation in the large intestine.* PLoS One, 2013. 8(7): p. e68952.
28. Atarashi, K., et al., *Treg induction by a rationally selected mixture of Clostridia strains from the human microbiota.* Nature, 2013. 500(7461): p. 232-6.
29. Smelt, M. J., et al., *The impact of Lactobacillus plantarum WCFS1 teichoic acid D-alanylation on the generation of effector and regulatory T-cells in healthy mice.* PLoS One, 2013. 8(4): p. e63099.
30. Qiu, X., et al., *Faecalibacterium prausnitzii upregulates regulatory T cells and anti-inflammatory cytokines in treating TNBS-induced colitis.* J Crohns Colitis, 2013. 7(11): p. e558-68.
31. Liu, Y., et al., *Lactobacillus reuteri DSM 17938 changes the frequency of Foxp3+ regulatory T cells in the intestine and mesenteric lymph node in experimental necrotizing enterocolitis.* PLoS One, 2013. 8(2): p. e56547.
32. Zhao, H. M., et al., *Probiotics increase T regulatory cells and reduce severity of experimental colitis in mice.* World J Gastroenterol, 2013. 19(5): p. 742-9.
33. Jeon, S. G., et al., *Probiotic Bifidobacterium breve induces IL-10-producing Tr1 cells in the colon.* PLoS Pathog, 2012. 8(5): p. e1002714.
34. Jang, S. O., et al., *Asthma Prevention by Lactobacillus Rhamnosus in a Mouse Model is Associated With CD4(+)CD25(+)Foxp3(+)T Cells.* Allergy Asthma Immunol Res, 2012. 4(3): p. 150-6.
35. Lopez, P., et al., *Interaction of Bifidobacterium bifidum LMG13195 with HT29 cells influences regulatory-T-cell-associated chemokine receptor expression.* Appl Environ Microbiol, 2012. 78(8): p. 2850-7.
36. Lopez, P., et al., *Treg-inducing membrane vesicles from Bifidobacterium bifidum LMG13195 as potential adjuvants in immunotherapy.* Vaccine, 2012. 30(5): p. 825-9.
37. Fink, L. N., *Induction of regulatory T cells by probiotics: potential for treatment of allergy?* Clin Exp Allergy, 2010. 40(1): p. 5-8.
38. Lavasani, S., et al., *A novel probiotic mixture exerts a therapeutic effect on experimental autoimmune encephalomyelitis mediated by IL-10 producing regulatory T cells.* PLoS One, 2010. 5(2): p. e9009.
39. Lyons, A., et al., *Bacterial strain-specific induction of Foxp3+ T regulatory cells is protective in murine allergy models.* Clin Exp Allergy, 2010. 40(5): p. 811-9.
40. de Roock, S., et al., *Lactic acid bacteria differ in their ability to induce functional regulatory T cells in humans.* Clin Exp Allergy, 2010. 40(1): p. 103-10.
41. Karimi, K., et al., *Lactobacillus reuteri-induced regulatory T cells protect against an allergic airway response in mice.* Am J Respir Crit Care Med, 2009. 179(3): p. 186-93.
42. Feleszko, W., et al., *Probiotic-induced suppression of allergic sensitization and airway inflammation is associated with an increase of T regulatory-dependent mechanisms in a murine model of asthma.* Clin Exp Allergy, 2007. 37(4): p. 498-505.
43. Lai, W. T., V. Krishnappa, and D. G. Phinney, *Fibroblast growth factor 2 (Fgf2) inhibits differentiation of mesenchymal stem cells by inducing Twist2 and Spry4, blocking extracellular regulated kinase activation, and altering Fgf receptor expression levels.* Stem Cells, 2011. 29(7): p. 1102-11.

44. Coutu, D. L., M. Francois, and J. Galipeau, *Inhibition of cellular senescence by developmentally regulated FGF receptors in mesenchymal stem cells.* Blood, 2011. 117(25): p. 6801-12.
45. Kinnaird, T., et al., *Local delivery of marrow-derived stromal cells augments collateral perfusion through paracrine mechanisms.* Circulation, 2004. 109(12): p. 1543-9.
46. Kinnaird, T., et al., *Marrow-derived stromal cells express genes encoding a broad spectrum of arteriogenic cytokines and promote in vitro and in vivo arteriogenesis through paracrine mechanisms.* Circ Res, 2004. 94(5): p. 678-85.
47. Kwon, H. M., et al., *Multiple paracrine factors secreted by mesenchymal stem cells contribute to angiogenesis.* Vascul Pharmacol, 2014. 63(1): p. 19-28.
48. Montes, R., et al., *Feeder-free maintenance of hESCs in mesenchymal stem cell-conditioned media: distinct requirements for TGF-beta and IGF-II.* Cell Res, 2009. 19(6): p. 698-709.
49. Shen, C., et al., *Conditioned medium from umbilical cord mesenchymal stem cells induces migration and angiogenesis.* Mol Med Rep, 2015. 12(1): p. 20-30.
50. Walenda, T., et al., *Synergistic effects of growth factors and mesenchymal stromal cells for expansion of hematopoietic stem and progenitor cells.* Exp Hematol, 2011. 39(6): p. 617-28.
51. Fong, C. Y., et al., *Human umbilical cord Wharton's jelly stem cells and its conditioned medium support hematopoietic stem cell expansion ex vivo.* J Cell Biochem, 2012. 113(2): p. 658-68.
52. Zou, Q., et al., *Development of a Xeno-Free Feeder-Layer System from Human Umbilical Cord Mesenchymal Stem Cells for Prolonged Expansion of Human Induced Pluripotent Stem Cells in Culture.* PLoS One, 2016. 11(2): p. e0149023.
53. Silva Dos Santos, D., et al., *Human Menstrual Blood-Derived Mesenchymal Cells as New Human Feeder Layer System for Human Embryonic Stem Cells.* Cell Med, 2014. 7(1): p. 25-35.
54. Cahill, E. F., et al., *Jagged-1 is required for the expansion of CD4+ CD25+ FoxP3+ regulatory T cells and tolerogenic dendritic cells by murine mesenchymal stromal cells.* Stem Cell Res Ther, 2015. 6: p. 19.
55. Wang, Z. X., et al., *Mesenchymal stem cells alleviate atherosclerosis by elevating number and function of CD4(+)CD25(+)FOXP3(+) regulatory T-cells and inhibiting macrophage foam cell formation.* Mol Cell Biochem, 2015. 400(1-2): p. 163-72.
56. Kwon, M. S., et al., *The immunomodulatory effects of human mesenchymal stem cells on peripheral blood mononuclear cells in ALS patients.* J Neurochem, 2014. 131(2): p. 206-18.
57. Luz-Crawford, P., et al., *Mesenchymal stem cells generate a CD4+CD25+Foxp3+ regulatory T cell population during the differentiation process of Th1 and Th17 cells.* Stem Cell Res Ther, 2013. 4(3): p. 65.
58. Erkers, T., et al., *Decidual stromal cells promote regulatory T cells and suppress alloreactivity in a cell contact-dependent manner.* Stem Cells Dev, 2013. 22(19): p. 2596-605.
59. Engela, A. U., et al., *Human adipose-tissue derived mesenchymal stem cells induce functional de-novo regulatory T cells with methylated FOXP3 gene DNA.* Clin Exp Immunol, 2013. 173(2): p. 343-54.
60. Bai, L., et al., *Hepatocyte growth factor mediates mesenchymal stem cell-induced recovery in multiple sclerosis models.* Nat Neurosci, 2012. 15(6): p. 862-70.
61. Lee, E. S., et al., *Adoptive Transfer of Treg Cells Combined with Mesenchymal Stem Cells Facilitates Repopulation of Endogenous Treg Cells in a Murine Acute GVHD Model.* PLoS One, 2015. 10(9): p. e0138846.
62. Treacy, O., et al., *Mesenchymal stem cell therapy promotes corneal allograft survival in rats by local and systemic immunomodulation.* Am J Transplant, 2014. 14(9): p. 2023-36.
63. Yu, B., et al., *Enhanced mesenchymal stem cell survival induced by GATA-4 overexpression is partially mediated by regulation of the miR-15 family.* Int J Biochem Cell Biol, 2013. 45(12): p. 2724-35.
64. Xu, W., et al., *Basic fibroblast growth factor expression is implicated in mesenchymal stem cells response to light-induced retinal injury.* Cell Mol Neurobiol, 2013. 33(8): p. 1171-9.
65. Fang, Z., et al., *Differentiation of GFP-Bcl-2-engineered mesenchymal stem cells towards a nucleus pulposus-like phenotype under hypoxia in vitro.* Biochem Biophys Res Commun, 2013. 432(3): p. 444-50.
66. Li, W., et al., *Bcl-2 engineered MSCs inhibited apoptosis and improved heart function.* Stem Cells, 2007. 25(8): p. 2118-27.
67. Tsubokawa, T., et al., *Impact of anti-apoptotic and anti-oxidative effects of bone marrow mesenchymal stem cells with transient overexpression of heme oxygenase-1 on myocardial ischemia.* Am J Physiol Heart Circ Physiol, 2010. 298(5): p. H1320-9.
68. Zhou, H., et al., *Exendin-4 protects adipose-derived mesenchymal stem cells from apoptosis induced by hydrogen peroxide through the PI3K/Akt-Sfrp2 pathways.* Free Radic Biol Med, 2014. 77: p. 363-75.
69. Le Blanc, K., et al., *Treatment of severe acute graft-versus-host disease with third party haploidentical mesenchymal stem cells.* Lancet, 2004. 363(9419): p. 1439-41.
70. Lazarus, H. M., et al., *Cotransplantation of HLA-identical sibling culture-expanded mesenchymal stem cells and hematopoietic stem cells in hematologic malignancy patients.* Biol Blood Marrow Transplant, 2005. 11(5): p. 389-98.
71. Bernardo, M. E., et al., *Optimization of in vitro expansion of human multipotent mesenchymal stromal cells for cell-therapy approaches: further insights in the search for a fetal calf serum substitute.* J Cell Physiol, 2007. 211(1): p. 121-30.
72. Reinisch, A., et al., *Humanized system to propagate cord blood-derived multipotent mesenchymal stromal cells for clinical application.* Regen Med, 2007. 2(4): p. 371-82.
73. Capelli, C., et al., *Human platelet lysate allows expansion and clinical grade production of mesenchymal stromal cells from small samples of bone marrow aspirates or marrow filter washouts.* Bone Marrow Transplant, 2007. 40(8): p. 785-91.
74. Lataillade, J. J., et al., *New approach to radiation burn treatment by dosimetry-guided surgery combined with autologous mesenchymal stem cell therapy.* Regen Med, 2007. 2(5): p. 785-94.
75. Seshareddy, K., D. Troyer, and M. L. Weiss, *Method to isolate mesenchymal-like cells from Wharton's Jelly of umbilical cord.* Methods Cell Biol, 2008. 86: p. 101-19.
76. Sensebe, L., *Clinical grade production of mesenchymal stem cells.* Biomed Mater Eng, 2008. 18(1 Suppl): p. S3-10.

77. Sotiropoulou, P. A., S. A. Perez, and M. Papamichail, *Clinical grade expansion of human bone marrow mesenchymal stem cells.* Methods Mol Biol, 2007. 407: p. 245-63.
78. Shetty, P., et al., *Clinical grade mesenchymal stem cells transdifferentiated under xenofree conditions alleviates motor deficiencies in a rat model of Parkinson's disease.* Cell Biol Int, 2009. 33(8): p. 830-8.
79. Zhang, X., et al., *Cotransplantation of HLA-identical mesenchymal stem cells and hematopoietic stem cells in Chinese patients with hematologic diseases.* Int J Lab Hematol, 2010. 32(2): p. 256-64.
80. Arrigoni, E., et al., *Isolation, characterization and osteogenic differentiation of adipose-derived stem cells: from small to large animal models.* Cell Tissue Res, 2009. 338(3): p. 401-11.
81. Grisendi, G., et al., *GMP-manufactured density gradient media for optimized mesenchymal stromal/stem cell isolation and expansion.* Cytotherapy, 2010. 12(4): p. 466-77.
82. Prasad, V. K., et al., *Efficacy and safety of ex vivo cultured adult human mesenchymal stem cells (Prochymal) in pediatric patients with severe refractory acute graft-versus-host disease in a compassionate use study.* Biol Blood Marrow Transplant, 2011. 17(4): p. 534-41.
83. Sensebe, L., P. Bourin, and K. Tarte, *Good manufacturing practices production of mesenchymal stem/stromal cells.* Hum Gene Ther, 2011. 22(1): p. 19-26.
84. Capelli, C., et al., *Minimally manipulated whole human umbilical cord is a rich source of clinical-grade human mesenchymal stromal cells expanded in human platelet lysate.* Cytotherapy, 2011. 13(7): p. 786-801.
85. Ilic, N., et al., *Manufacture of clinical grade human placenta-derived multipotent mesenchymal stromal cells.* Methods Mol Biol, 2011. 698: p. 89-106.
86. Santos, F., et al., *Toward a clinical-grade expansion of mesenchymal stem cells from human sources: a microcarrier-based culture system under xeno-free conditions.* Tissue Eng Part C Methods, 2011. 17(12): p. 1201-10.
87. Timmins, N. E., et al., *Closed system isolation and scalable expansion of human placental mesenchymal stem cells.* Biotechnol Bioeng, 2012. 109(7): p. 1817-26.
88. Warnke, P. H., et al., *A clinically feasible protocol for using human platelet lysate and mesenchymal stem cells in regenerative therapies.* J Craniomaxillofac Surg, 2013. 41(2): p. 153-61.
89. Fekete, N., et al., *GMP-compliant isolation and large-scale expansion of bone marrow-derived MSC.* PLoS One, 2012. 7(8): p. e43255.
90. Hanley, P. J., et al., *Manufacturing mesenchymal stromal cells for phase I clinical trials.* Cytotherapy, 2013. 15(4): p. 416-22.
91. Trojahn Kolle, S. F., et al., *Pooled human platelet lysate versus fetal bovine serum-investigating the proliferation rate, chromosome stability and angiogenic potential of human adipose tissue-derived stem cells intended for clinical use.* Cytotherapy, 2013. 15(9): p. 1086-97.
92. Veronesi, E., et al., *Transportation conditions for prompt use of ex vivo expanded and freshly harvested clinical-grade bone marrow mesenchymal stromal/stem cells for bone regeneration.* Tissue Eng Part C Methods, 2014. 20(3): p. 239-51.
93. Dolley-Sonneville, P. J., L. E. Romeo, and Z. K. Melkoumian, *Synthetic surface for expansion of human mesenchymal stem cells in xeno-free, chemically defined culture conditions.* PLoS One, 2013. 8(8): p. e70263.
94. Siciliano, C., et al., *Optimization of the isolation and expansion method of human mediastinal-adipose tissue derived mesenchymal stem cells with virally inactivated GMP-grade platelet lysate.* Cytotechnology, 2015. 67(1): p. 165-74.
95. Martins, J. P., et al., *Towards an advanced therapy medicinal product based on mesenchymal stromal cells isolated from the umbilical cord tissue: quality and safety data.* Stem Cell Res Ther, 2014. 5(1): p. 9.
96. Iudicone, P., et al., *Pathogen-free, plasma-poor platelet lysate and expansion of human mesenchymal stem cells.* J Transl Med, 2014. 12: p. 28.
97. Skrahin, A., et al., *Autologous mesenchymal stromal cell infusion as adjunct treatment in patients with multidrug and extensively drug-resistant tuberculosis: an open-label phase 1 safety trial.* Lancet Respir Med, 2014. 2(2): p. 108-22.
98. Ikebe, C. and K. Suzuki, *Mesenchymal stem cells for regenerative therapy: optimization of cell preparation protocols.* Biomed Res Int, 2014. 2014: p. 951512.
99. Chatzistamatiou, T. K., et al., *Optimizing isolation culture and freezing methods to preserve Wharton's jelly's mesenchymal stem cell (MSC) properties: an MSC banking protocol validation for the Hellenic Cord Blood Bank.* Transfusion, 2014. 54(12): p. 3108-20.
100. Swamynathan, P., et al., *Are serum free and xeno-free culture conditions ideal for large scale clinical grade expansion of Wharton's jelly derived mesenchymal stem cells? A comparative study.* Stem Cell Res Ther, 2014. 5(4): p. 88.
101. Vaes, B., et al., *Culturing protocols for human multipotent adult stem cells.* Methods Mol Biol, 2015. 1235: p. 49-58.
102. Devito, L., et al., *Wharton's jelly mesenchymal stromal/stem cells derived under chemically defined animal product free low oxygen conditions are rich in MSCA-1(+) subpopulation.* Regen Med, 2014. 9(6): p. 723-32.

The invention claimed is:
1. A method of stimulating an increase in perfusion of the lower back area comprising the steps of: a) identifying a patient with a perfusion defect in said lower back area; b) administering a population of T regulatory cells that have been activated by exposure to anti-CD3 and anti-CD28 antibodies into muscles surrounding the lower back area at a concentration and frequency sufficient to induce an angiogenic response.
2. The method of claim 1, wherein said T regulatory cells are allogeneic.
3. The method of claim 2, wherein said T regulatory cells are autologous.
4. The method of claim 1, wherein said T regulatory cells are derived from peripheral blood mononuclear cells.
5. The method of claim 1, wherein said T regulatory cells are derived from mobilized peripheral blood mononuclear cells.
6. The method of claim 5, wherein said mobilization is achieved by administration of one or more of the following agents: a) G-CSF; b) Flt-3 ligand; c) Thrombopoietin.
7. The method of claim 1, wherein said T regulatory cells are derived cord blood.
8. The method of claim 1, wherein said T regulatory cells are derived from adipose stromal vascular fraction cells.
9. The method of claim 1, wherein said T regulatory cells possesses expression of GITR ligand.
10. The method of claim 1, wherein said T regulatory cell expresses neuropilin-1.

11. The method of claim 1, wherein said T regulatory cells are activated by exposure to mesenchymal stem cell conditioned media.

12. The method of claim 1, wherein said T regulatory cells are activated by exposure to mesenchymal stem cell derived exosomes.

13. The method of claim 1, wherein said T regulatory cells are activated by exposure to one or more of the following agents selected from the group consisting of: a) VEGF, and b) Hypoxic conditions.

14. The method of claim 1, wherein said T regulatory cells express FoxP3.

15. The method of claim 1, wherein said T regulatory cells are activated by culture with mesenchymal stem cells.

16. The method of claim 15, wherein said mesenchymal stem cells are obtained from a source selected from the group of tissues consisting of: a) adipose from the stromal vascular fraction; b) bone marrow; c) tooth pulp; d) hair follicle; e) endometrium; f) menstrual blood; g) peripheral blood; h) omentum; i) skin; j) cord blood; k) Wharton's jelly; l) placenta; and m) fallopian tube.

17. The method of claim 16, wherein said adipose derived mesenchymal stem cells are in vitro-expanded purified mesenchymal stem cells possessing the markers: a) CD90; b) CD105 and c) CD73.

18. The method of claim 16, wherein, wherein said adipose derived cells are positively selected for a marker selected from the group consisting of: a) CD105; b) CD73; c) CD44; d) CD90; e) VEGFR2; and f) TEM-1.

19. The method of claim 1, wherein mesenchymal stem cells are administered together with said T regulatory cells to enhance angiogenesis.

20. The method of claim 1, wherein said cell administration into said muscles surrounding the lower back is performed by intramuscular administration into muscles in the lumbar area selected from the group consisting of: a) Multifidus muscles; b) Psoas muscles; c) Transversospinalis muscles; d) Sacrospinalis muscles.

* * * * *